(12) United States Patent
Taguchi et al.

(10) Patent No.: US 7,741,454 B2
(45) Date of Patent: Jun. 22, 2010

(54) BIOLOGICAL LOW-MOLECULAR-WEIGHT DERIVATIVES

(75) Inventors: Tetsushi Taguchi, Tsukuba (JP); Hisatoshi Kobayashi, Tsukuba (JP); Junzo Tanaka, Tsukuba (JP); Hirofumi Saito, Tokyo (JP)

(73) Assignees: National Institute for Materials Science, Tsukuba-shi (JP); Furuuchi Chemical Corporation, Tokyo (JP)

( * ) Notice: Subject to any disclaimer, the term of this patent is extended or adjusted under 35 U.S.C. 154(b) by 573 days.

(21) Appl. No.: 10/527,694

(22) PCT Filed: Sep. 11, 2003

(86) PCT No.: PCT/JP03/11669

§ 371 (c)(1),
(2), (4) Date: Nov. 1, 2005

(87) PCT Pub. No.: WO2004/024686

PCT Pub. Date: Mar. 25, 2004

(65) Prior Publication Data

US 2006/0128948 A1 Jun. 15, 2006

(30) Foreign Application Priority Data

Sep. 11, 2002 (JP) .............................. 2002-265982

(51) Int. Cl.
| | | |
|---|---|---|
| C07K 1/00 | (2006.01) | |
| C07K 14/00 | (2006.01) | |
| C07K 17/00 | (2006.01) | |
| C07K 16/00 | (2006.01) | |
| C08H 1/00 | (2006.01) | |
| A61F 2/00 | (2006.01) | |
| A61K 31/74 | (2006.01) | |
| A61F 13/15 | (2006.01) | |
| A61F 13/20 | (2006.01) | |

(52) U.S. Cl. .................... 530/402; 424/422; 424/78.27; 514/801; 604/368

(58) Field of Classification Search ................. 530/402; 424/422, 78.27; 514/801; 604/368
See application file for complete search history.

(56) References Cited

U.S. PATENT DOCUMENTS

| 4,757,140 A | * | 7/1988 | DeLuca et al. ........... 536/26.23 |
| 5,324,775 A | | 6/1994 | Rhee et al. |
| 5,328,955 A | | 7/1994 | Rhee et al. |
| 5,752,974 A | * | 5/1998 | Rhee et al. .................. 606/214 |
| 6,166,130 A | * | 12/2000 | Rhee et al. ................. 525/54.1 |
| 7,129,209 B2 | * | 10/2006 | Rhee ............................ 514/2 |

FOREIGN PATENT DOCUMENTS

| JP | 61-69759 | | 4/1986 |
| JP | 07-163650 | | 6/1995 |
| JP | 8-53548 | | 2/1996 |
| JP | 09-249751 | | 9/1997 |
| JP | 10-71199 | | 3/1998 |
| JP | 2 000-212286 | * | 8/2000 |
| WO | WO-97/22371 | | 6/1997 |
| WO | WO-01/91814 A2 | | 12/2001 |

OTHER PUBLICATIONS

Milewska, MJ, Chimiak, A, Glowacki, Z (1987) Synthesis of schizokinen, homoschizokinen, its imide and the detection of imide with 13C-NMR-spectroscopy. J. Prakt. Chem., 329(3), 44-456.*
Hermanson, G.T. (1996) "Zero-Length Cross-linkers" in Bioconjugate Techniques, p. 169-186, Academic Press, Elsevier.*
T. Sakamoto et al.; Journal of Organic Chemistry, 1996, 61 (24), pp. 8496-8499. Cited in the int'l. search report.
H. H. Olde Damink et al.; Biomaterials, vol. 17, Issue 8, 1996, pp. 765-773.

* cited by examiner

*Primary Examiner*—Shaojia Anna Jiang
*Assistant Examiner*—Scarlett Goon
(74) *Attorney, Agent, or Firm*—Westerman, Hattori, Daniels & Adrian, LLP

(57) ABSTRACT

The crosslinking agents and condensing agents that have been employed in biological adhesives and in treating medical devices such as cardiac valves are non-natural compounds synthesized artificially. Thus, they are not metabolized in vivo and exhibit toxicity to living bodies. These compounds are thus used only in a restricted amount and for limited purposes in the clinical sites. The present invention provides a biological low-molecular-weight derivative obtained by modifying carboxyl groups of a biological low-molecular-weight compound with N-hydroxysuccinimide, N-hydroxysulfosuccinimide, or a derivative thereof and a crosslinked high-molecular-weight product obtained by crosslinking various high-molecular-weight compounds with this derivative.

2 Claims, 1 Drawing Sheet

BIOLOGICAL LOW-MOLECULAR-WEIGHT DERIVATIVES

TECHNICAL FIELD

The present invention relates to biological low-molecular-weight derivatives obtained by modifying carboxyl groups of biological low-molecular-weight compounds having two or more carboxyl groups with N-hydroxysuccinimide, N-hydroxysulfosuccinimide, or derivatives thereof, and to crosslinked high-molecular-weight products synthesized using the biological low-molecular-weight derivatives.

BACKGROUND ART

In biological adhesives and in treating medical devices that are derived from biological compounds, such as porcine cardiac valves, crosslinking agents containing artificially and chemically synthesized aldehydes such as glutaraldehyde or condensing agents such as 1-ethyl-3-(3-dimethylaminopropyl)carbodiimide have been used (for example, refer to patent documents 1 to 6, and non-patent document 1).
Patent document 1: Japanese Unexamined Patent Application Publication No. 7-163650
Patent document 2: Japanese Unexamined Patent Application Publication No. 9-249751
Patent document 3: Japanese Unexamined Patent Application Publication No. 10-71199
Patent document 4: PCT Japanese Translation Patent Publication No. 2000-502380
Patent document 5: Japanese Unexamined Patent Application Publication No. 8-53548
Patent document 6: PCT Japanese Translation Patent Publication No. 8-502082
Non-patent document 1: Biomaterials, vol. 17, p. 765 (1996)

DISCLOSURE OF INVENTION

Most crosslinking agents and condensing agents that have been used to treat medical devices and the like are non-natural, artificially synthesized products. Thus, they are not metabolized in vivo and exhibit toxicity to living bodies. They are thus used in limited amounts and for limited purposes in clinical sites. In order to overcome such problems, development of biological crosslinking agents is desired.

The present invention provides a biological low-molecular-weight derivative obtained by modifying carboxyl groups of a biological low-molecular-weight compound having two or more carboxyl groups with N-hydroxysuccinimide, N-hydroxysulfosuccinimide, or a derivative thereof, and a crosslinked high-molecular weight product synthesized using the biological low-molecular-weight derivative.

In detail, the present invention provides a biological low-molecular-weight derivative obtained by modifying at least one carboxyl group of a biological low-molecular-weight compound having two or more carboxyl groups with N-hydroxysuccinimide, N-hydroxysulfosuccinimide, or a derivative thereof. This biological low-molecular-weight derivative is harmless to human bodies and achieves fast reaction since two or more reactive groups (—COOH) are contained.

The present invention also provides a crosslinked high-molecular weight product prepared by crosslinking a high-molecular-weight compound with a biological low-molecular-weight derivative obtained by modifying at least one carboxyl group of a biological low-molecular-weight compound having two or more carboxyl groups with N-hydroxysuccinimide, N-hydroxysulfosuccinimide, or a derivative thereof.

When this crosslinked high-molecular weight product is applied to living bodies, the compound is metabolized in vivo, and is absorbed and disappears after a predetermined time. Thus, no extraneous matter remains in the body.

BEST MODE FOR CARRYING OUT THE INVENTION

Figure 1:
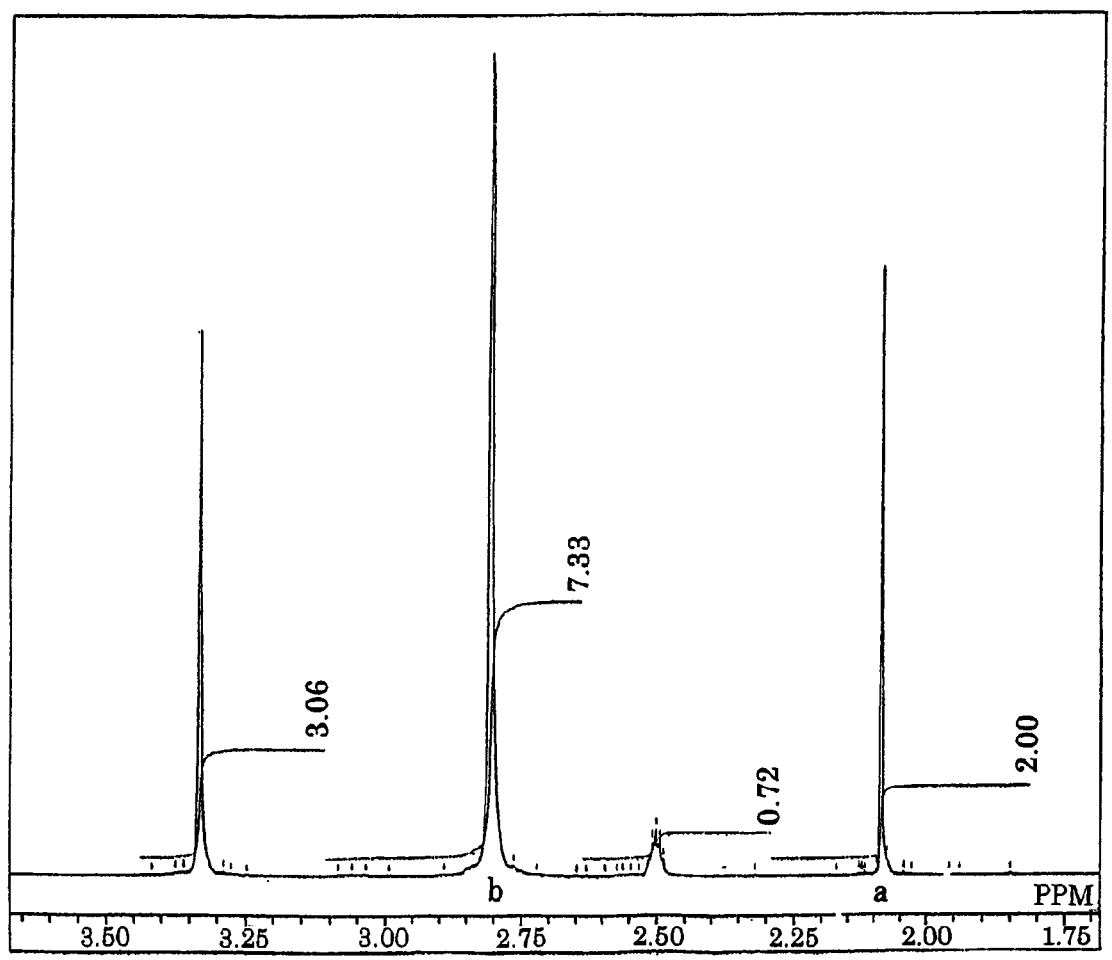
FIG. 1 is a chart showing a nuclear magnetic resonance spectrum of a citric acid derivative.

A biological low-molecular-weight compound having two or more carboxyl groups used in the present invention is a tri- or dicarboxylic acid low-molecular-weight compound in the citric acid cycle. Examples of the tri- or dicarboxylic acid low-molecular-weight compound include malic acid, oxalacetic acid, citric acid, cis-aconitic acid, 2-ketoglutaric acid, and derivatives thereof.

The biological low-molecular-weight derivative of the present invention is obtained by reacting carboxyl groups of the biological low-molecular-weight compound having two or more carboxyl groups with N-hydroxysuccinimide, N-hydroxysulfosuccinimide, or a derivative thereof having low cytotoxicity in the presence of carbodiimide to introduce active esters.

Such a compound is obtained by reacting 0.001 to 10 percent by weight of the biological low-molecular-weight compound with 0.001 to 10 percent by weight of N-hydroxysuccinimide, N-hydroxysulfosuccinimide, or a derivative thereof in the presence of 0.001 to 20 percent by weight of carbodiimide (EDC) at a suitable reaction temperature in the range of 0° C. to 100° C. and a reaction time in the range of 1 to 48 hours.

Examples of the carbodiimide include 1-ethyl-3-(3-dimethylaminopropyl)carbodiimide hydrochloride (EDC), 1-cyclohexyl-3-(2-morpholinoethyl)carbodiimide metho-p-toluenesulfonate, and dicyclohexylcarbodiimide. Examples of the reaction solvent include N,N-dimethylformamide (DMF) and dimethylsulfoxide (DMSO).

FIG. 1 is a chart showing a nuclear magnetic resonance spectrum of a citric acid derivative yielded by the reaction between citric acid and N-hydroxysuccinimide in the presence of EDC. The peak a shows the methylene proton of citric acid and the peak b shows the methylene proton of the succinimidyl group. The remaining two peaks are attributable to the solvent (DMSO).

Examples of the protein used in preparing the crosslinked compound include collagen (any of several ten types), atelocollagen (any one of several ten types), alkali-soluble collagen (any of several ten types), gelatin, keratin, serum albumin, egg albumin, hemoglobin, casein, and amino-containing polymers such as globulin and fibrinogen. These proteins may be derived from any organism.

Examples of glycosaminoglycans used to prepare the crosslinked product include chondroitin sulfate, dermatan sulfate, hyaluronic acid, heparan sulfate, heparin, keratan sulfate, and their derivatives. The glycosaminoglycans may have any molecular weight and may be derived from any organism.

Examples of other high-molecular-weight compounds include chitosan (the degree of deacetylation and molecular weight are not limited), polyamino acids (the type of amino acid and molecular weight are not limited), and polyalcohols (the type and molecular weight are not limited).

The crosslinking reaction between the biological low-molecular-weight derivative and the high-molecular-weight compound is conducted by reacting 0.1 to 50 percent by weight of the high-molecular-weight compound with 0.01 to 50 percent by weight of the biological low-molecular-weight derivative at preferably 30° C. to 50° C. These two compounds are preferably mixed as solutions having predetermined concentrations to facilitate synthesis of a homogeneous crosslinked product. Examples of the solvents used to prepare such solutions include nontoxic solvents such as distilled water, buffer solutions, e.g., physiological saline, sodium hydrogen carbonate, boric acid, and phosphoric acid, and organic solvents (DMF, DMSO, and ethanol).

EXAMPLES

Example 1-1

To a 5 wt % DMF solution of citric acid, 3.2 equivalents of N-hydroxysuccinimide and 3.1 equivalents of EDC were added at room temperature, and the resulting mixture was stirred for 24 hours. Subsequently, only the DMF, i.e., the organic solvent in the reaction solution, was removed by reduced-pressure distillation. The residue was purified with an acetone/n-hexane developing solvent by chromatography over a silica gel column to synthesize a derivative having three carboxyl groups of citric acid modified with N-hydroxysuccinimide.

Example 1-2

The synthesis of collagen gel obtained by the reaction scheme below using the citric acid derivative synthesized in Example 1-1 will now be described:

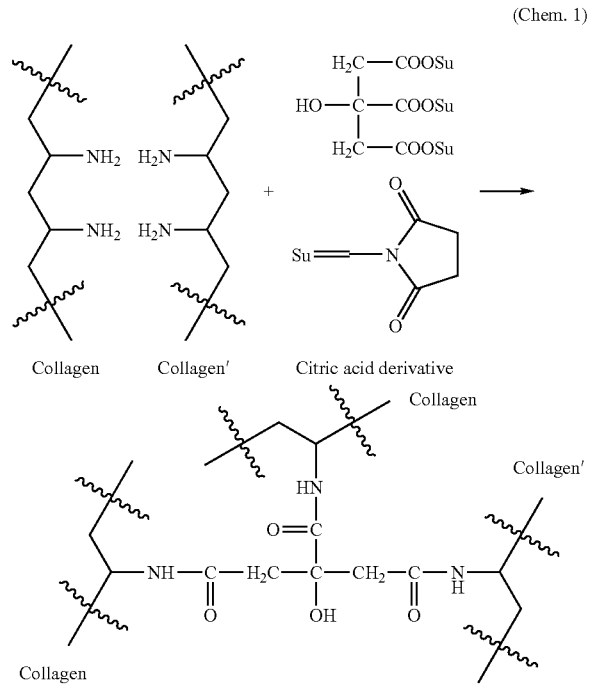

(Chem. 1)

The synthesized citric acid derivative (24 μL) was dissolved in 976 μL of a dimethylsulfoxide solution. A 100 μL portion of this solution was weighed and added to 400 μL of a 1.25 wt % phosphoric acid buffer solution of type II collagen. The resulting mixture was stirred and left to stand still for 24 hours at room temperature to obtain a collagen gel having a crosslinking agent concentration of 0.4 to 40 mM. The gel was weighed, dried in a freeze-dry machine, and weighed again to determine the water content of the gel. The water content of the gel is shown in Table 1.

TABLE 1

| Concentration of citric acid derivative (mM) | Water content (%) |
|---|---|
| 0.4 | 98 |
| 1 | 98 |
| 2 | 96 |
| 4 | 97 |
| 8 | 97 |
| 10 | 97 |
| 20 | 98 |
| 30 | 98 |
| 40 | 98 |

Example 2-1

To a 5 wt % DMF solution of 2-ketoglutaric acid, 2.2 equivalents of N-hydroxysuccinimide and 2.1 equivalents of EDC were added at room temperature. The resulting mixture was stirred for 24 hours. Subsequently, only the DMF, i.e., the organic solvent in the reaction solution, was removed by reduced-pressure distillation. The residue was purified with an acetone/n-hexane developing solvent by chromatography over a silica gel column to obtain a derivative having two carboxyl groups of 2-ketoglutaric acid modified with N-hydroxysuccinimide.

Example 2-2

The synthesis of collagen gel obtained by the reaction scheme below using the 2-ketoglutaric acid derivative synthesized in Example 2-1 will now be described:

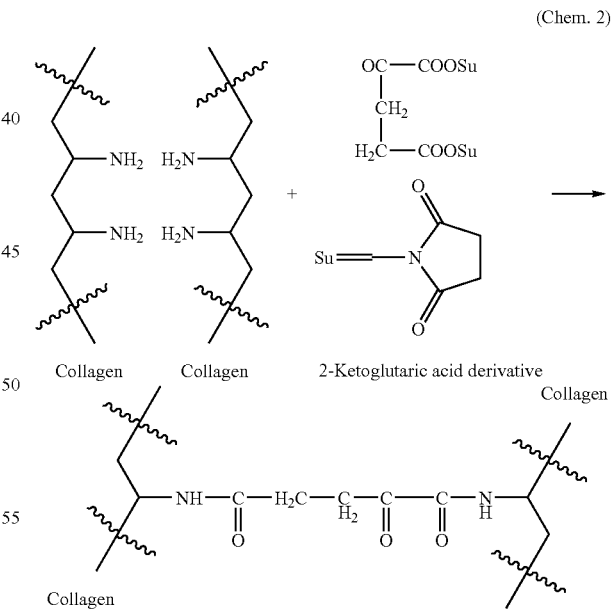

(Chem. 2)

The synthesized 2-ketoglutaric acid derivative (14 μL) was dissolved in 986 μL of a dimethylsulfoxide solution. A 100 μL portion of this solution was weighed and added to 400 μL of a 1.25 wt % phosphoric acid buffer solution of type II collagen. The resulting mixture was stirred and left to stand still for 24 hours at room temperature to obtain a collagen gel having a crosslinking agent concentration of 0.6 to 10 mM. The gel was weighed, dried in a freeze-dry machine, and weighed again to determine the water content of the gel. The water content of the gel is shown in Table 2.

TABLE 2

| Concentration of 2-ketogluraic acid derivative (Mm) | Water content (%) |
|---|---|
| 0.6 | 98 |
| 0.8 | 98 |
| 1 | 98 |
| 4 | 97 |
| 8 | 98 |
| 10 | 97 |

Example 3-1

To a 5 wt % DMF solution of cis-aconitic acid, 3.2 equivalents of N-hydroxysuccinimide and 3.1 equivalents of EDC were added at room temperature. The resulting mixture was stirred for 24 hours. Subsequently, only the DMF, i.e., the organic solvent in the reaction solution, was removed by reduced-pressure distillation. The residue was purified with an acetone/n-hexane developing solvent by chromatography over a silica gel column to obtain a derivative having three carboxyl groups of cis-aconitic acid modified with N-hydroxysuccinimide.

Example 3-2

The synthesis of collagen gel obtained by the reaction scheme below using the cis-aconitic acid derivative synthesized in Example 3-1 will now be described:

portion of this solution was weighed and added to 400 μL of a 1.25 wt % phosphoric acid buffer solution of type II collagen. The resulting mixture was stirred and left to stand still for 24 hours at room temperature to obtain a collagen gel having a crosslinking agent concentration of 1 to 30 mM. The gel was weighed, dried in a freeze-dry machine, and weighed again to determine the water content of the gel. The water content of the gel is shown in Table 3.

TABLE 3

| Concentration of cis-aconitic acid derivative (mM) | Water content (%) |
|---|---|
| 1 | 97 |
| 2 | 97 |
| 4 | 97 |
| 8 | 97 |
| 10 | 97 |
| 30 | 97 |

Example 4-1

To a 5 wt % DMF solution of malic acid, 2.2 equivalents of N-hydroxysuccinimide and 2.1 equivalents of EDC were added at room temperature. The resulting mixture was stirred for 24 hours. Subsequently, only the DMF, i.e., the organic solvent in the reaction solution, was removed by reduced-pressure distillation. The residue was purified with an acetone/n-hexane developing solvent by chromatography over a silica gel column to obtain a derivative having two carboxyl groups of malic acid modified with N-hydroxysuccinimide.

The synthesis of collagen gel obtained by the reaction scheme below using the malic acid derivative synthesized in Example 4-1 will now be described:

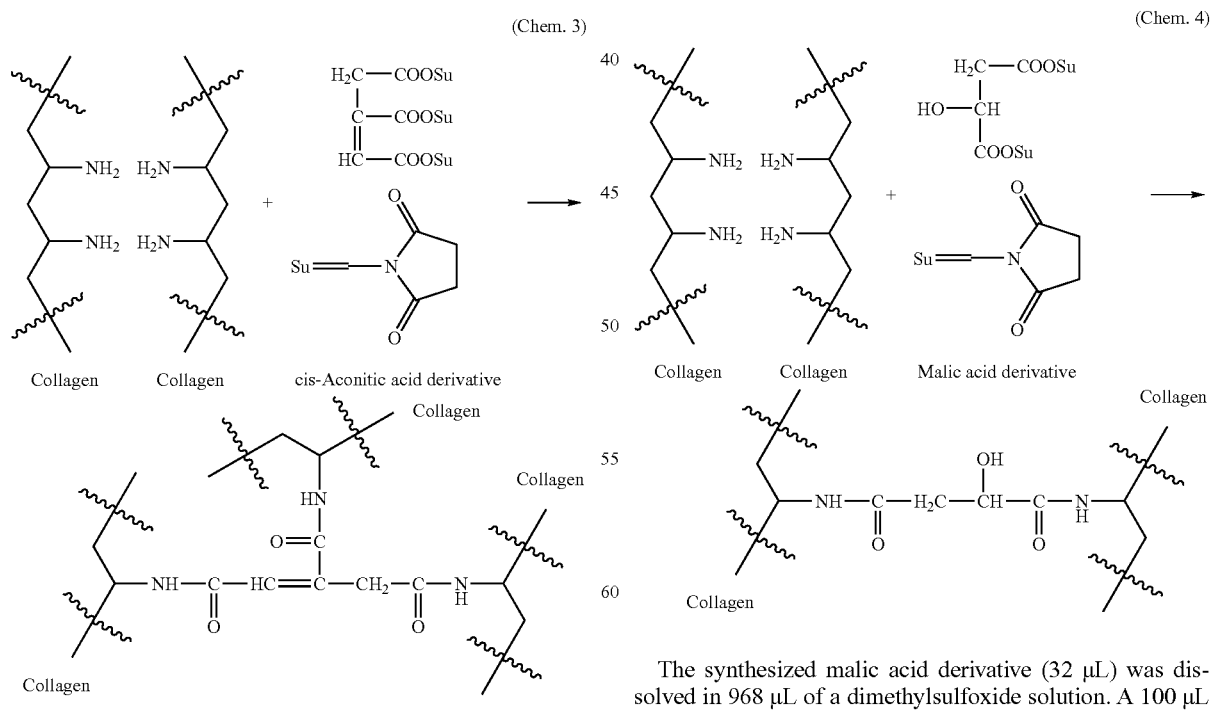

The synthesized cis-aconitic acid derivative (46 μL) was dissolved in 954 μL of a dimethylsulfoxide solution. A 100 μL The synthesized malic acid derivative (32 μL) was dissolved in 968 μL of a dimethylsulfoxide solution. A 100 μL portion of this solution was weighed and added to 400 μL of a 1.25 wt % phosphoric acid buffer solution of type II collagen. The resulting mixture was stirred and left to stand still for 24 hours at room temperature to obtain a collagen gel having a crosslinking agent concentration of 3 to 50 mM. The gel was weighed, dried in a freeze-dry machine, and weighed again to determine the water content of the gel. The water content of the gel is shown in Table 4.

TABLE 4

| Concentration of malic acid derivative (mM) | Water content (%) |
|---|---|
| 3 | 97 |
| 4 | 98 |
| 5 | 97 |
| 6 | 97 |
| 8 | 97 |
| 10 | 97 |
| 20 | 97 |
| 40 | 97 |
| 50 | 97 |

Example 5-1

To a 5 wt % DMF solution of oxalacetic acid, 2.2 equivalents of N-hydroxysuccinimide and 2.1 equivalents of EDC were added at room temperature. The resulting mixture was stirred for 24 hours. Subsequently, only the DMF, i.e., the organic solvent in the reaction solution, was removed by reduced-pressure distillation. The residue was purified with an acetone/n-hexane developing solvent by chromatography over a silica gel column to obtain a derivative having two carboxyl groups of oxalacetic acid modified with N-hydroxysuccinimide.

Example 5-2

The synthesis of collagen gel obtained by the reaction scheme below using the oxalacetic acid derivative synthesized in Example 5-1 will now be described:

(Chem. 5)

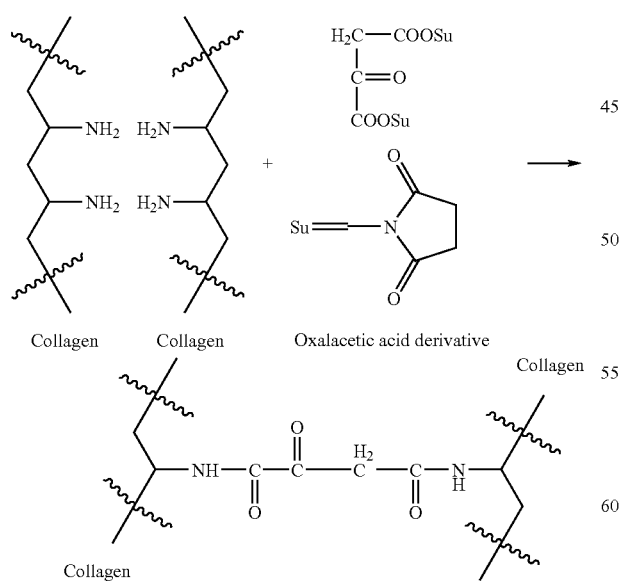

The synthesized oxalacetic acid derivative (16 μL) was dissolved in 984 μL of a dimethylsulfoxide solution. A 100 μL portion of this solution was weighed and added to 400 μL of a 1.25 wt % phosphoric acid buffer solution of type II collagen. The resulting mixture was stirred and left to stand still for 24 hours at room temperature to obtain a collagen gel having a crosslinking agent concentration of 2 to 40 mM. The gel was weighed, dried in a freeze-dry machine, and weighed again to determined the water content of the gel. The water content of the gel is shown in Table 5.

TABLE 5

| Concentration of oxalacetic acid derivative (mM) | Water content (%) |
|---|---|
| 2 | 98 |
| 4 | 97 |
| 6 | 98 |
| 8 | 97 |
| 10 | 98 |
| 20 | 96 |
| 40 | 98 |

INDUSTRIAL APPLICABILITY

The gelate biological high-molecular-weight product described above is applied to one of biological adhesives, hemostatic agents, materials for embolizing blood vessels, and sealing materials for aneurysum to perform crosslinking reaction directly at affected sites. The compound may be crosslinked in advance and then be applied to adhesion preventing agents, scaffolds for tissue regeneration, and drug carriers.

The invention claimed is:

1. A crosslinked high-molecular-weight product obtained by crosslinking a high-molecular-weight compound with a biological low-molecular-weight compound, the crosslinked high-molecular-weight product comprising a gel that is metabolized in vivo after application in vivo,
   wherein the high-molecular-weight compound is collagen,
   wherein the biological low-molecular-weight compound is obtained by modifying at least one carboxyl group of malic acid, oxalacetic acid, citric acid, cis-aconitic acid or 2-ketoglutaric acid with N-hydroxysuccinimide or N-hydroxysulfosuccinimide,
   wherein the crosslinked high-molecular-weight product has a water content of 96 to 98%, and
   wherein the crosslinked high-molecular-weight product has a chemical formula selected from the group consisting of:

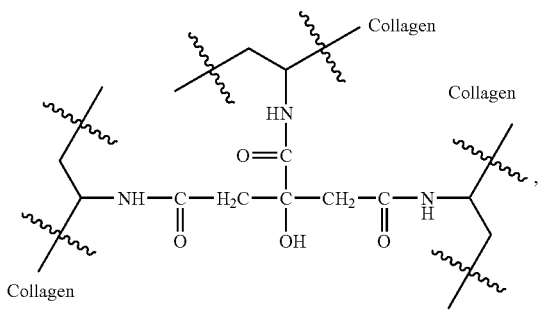

-continued

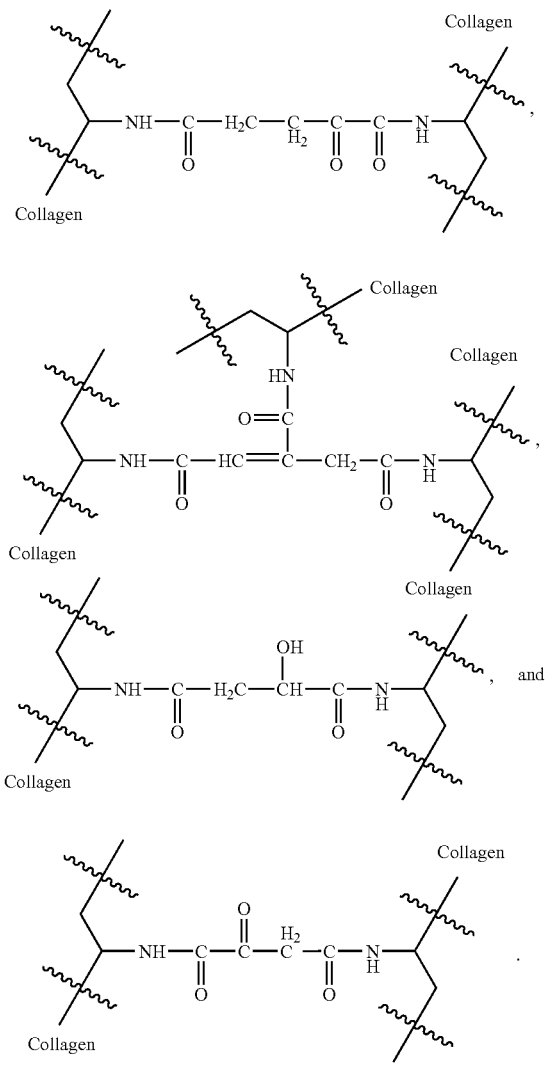

2. A method for producing a crosslinked high-molecular-weight product comprising:
reacting 0.001 to 10 percent by weight of malic acid, oxalacetic acid, citric acid, or cis-aconitic acid with 0.001 to 10 percent by weight of N-hydroxysuccinimide or N-hydroxysulfosuccinimide in the presence of 0.001 to 20 percent by weight of carbodiimide at a reaction temperature of 000 to 10000 for a reaction time of 1 to 48 hours to modify at least one carboxyl group of the malic acid, oxalacetic acid, citric acid cis-aconitic acid, or 2-ketoglutaric acid with N-hydroxysuccinimide or N-hydroxysulfosuccinimide to obtain a biological low-molecular-weight compound; and
crosslinking a high-molecular-weight compound with the biological low-molecular-weight compound so as to yield a crosslinked high-molecular-weight product comprising a gel that is metabolized in vivo after application in vivo wherein the high-molecular-weight compound is collagen,
wherein the crosslinked high-molecular-weight product has a water content of 96 to 98%, and
wherein the crosslinked high-molecular-weight product has a chemical formula selected from the group consisting of:

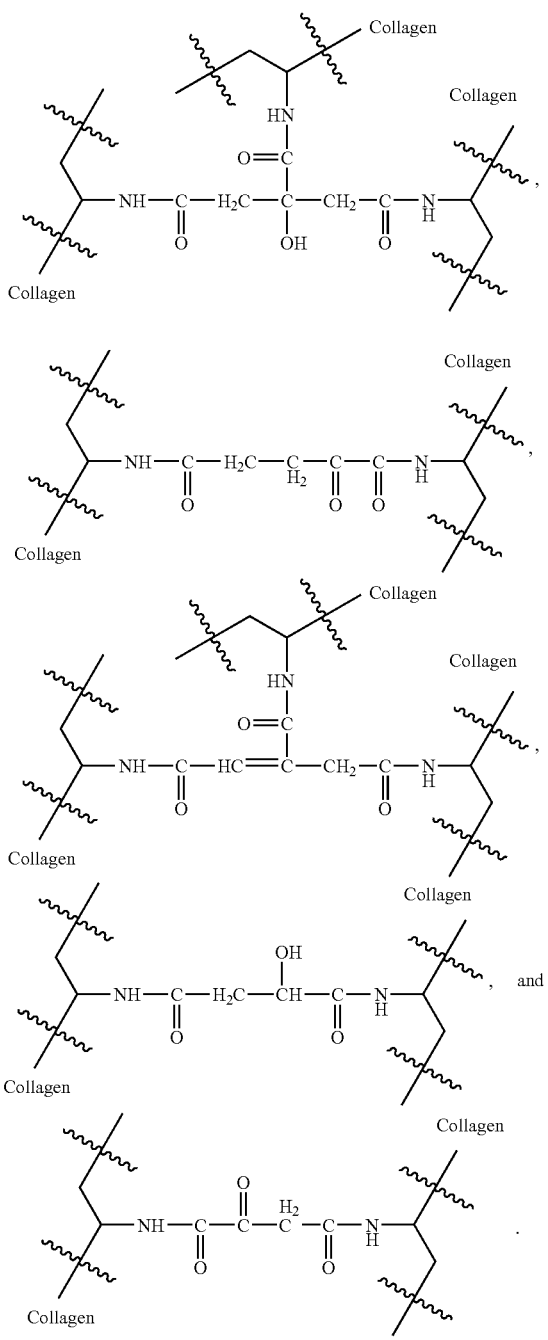

* * * * *